(12) United States Patent
Takada et al.

(10) Patent No.: US 6,777,931 B1
(45) Date of Patent: Aug. 17, 2004

(54) METHOD OF DISPLAYING SIGNAL OBTAINED BY MEASURING PROBE AND DEVICE THEREFOR

(75) Inventors: Hajime Takada, Chiba (JP); Ryouichi Sugimoto, Chiba (JP); Ikuo Yarita, Chiba (JP)

(73) Assignee: Kawasaki Steel Corporation, Kobe (JP)

( * ) Notice: Subject to any disclaimer, the term of this patent is extended or adjusted under 35 U.S.C. 154(b) by 0 days.

(21) Appl. No.: 09/446,916

(22) PCT Filed: May 11, 1999

(86) PCT No.: PCT/JP99/02419

§ 371 (c)(1),
(2), (4) Date: Dec. 29, 1999

(87) PCT Pub. No.: WO99/58967

PCT Pub. Date: Nov. 18, 1999

(30) Foreign Application Priority Data

May 12, 1998 (JP) ............................................ 10-128913

(51) Int. Cl.$^7$ ........................ G01N 27/82; G01N 29/04; G09G 5/06

(52) U.S. Cl. ........................ 324/240; 324/226; 324/238; 382/152; 382/165; 73/598; 73/600

(58) Field of Search ................................. 324/226, 227, 324/229–233, 235, 237, 238, 240–242, 262; 73/598, 600, 609–612; 382/152, 165; 345/22

(56) References Cited

U.S. PATENT DOCUMENTS

| | | | | |
|---|---|---|---|---|
| 4,439,730 A | * | 3/1984 | Kauffman | 324/232 |
| 4,644,336 A | * | 2/1987 | Mark, Jr. | 345/440.1 |
| 4,706,185 A | | 11/1987 | Karaki et al. | |
| 4,990,851 A | * | 2/1991 | Spies | 324/240 |
| 5,006,722 A | | 4/1991 | Adelson | |
| 5,006,800 A | * | 4/1991 | Hedengren et al. | 324/233 |
| 5,017,869 A | * | 5/1991 | Oliver | 324/230 |
| 5,030,911 A | | 7/1991 | Lam | |
| 5,345,514 A | * | 9/1994 | Mahdavieh et al. | 324/240 X |
| 5,430,376 A | | 7/1995 | Viertl | |
| 6,018,999 A | * | 2/2000 | Woodmansee et al. | 73/609 |
| 6,720,775 B2 | * | 4/2004 | Plotnikov et al. | 324/529 |

FOREIGN PATENT DOCUMENTS

| | | |
|---|---|---|
| JP | A-59-111056 | 6/1984 |
| JP | A-5-80034 | 3/1993 |
| JP | A-5-142215 | 6/1993 |
| JP | A-9-80030 | 3/1997 |
| WO | WO 97/43733 | 11/1997 |

OTHER PUBLICATIONS

David G. Daut and Dongming Zhao, A Flaw Detection method Based on Morphological Image Processing, IEEE Transactions on Circuits and Systems for Video Technology, vol. 3, No. 6, Dec. 1993, pp. 389–398.*

Hanshaw et al., Analysis of Ultrasonic Non Destructive Evaluation Data Using Singular Value Decomposition of the Hankel Data Matrix, Proceedings of the American Control Conference, Arlington, VA, Jun. 25–27, 2001, pp. 3672–3677.*

* cited by examiner

Primary Examiner—N. Le
Assistant Examiner—Darrell Kinder
(74) Attorney, Agent, or Firm—Oliff & Berridge PLC

(57) ABSTRACT

The testing results, etc. of surface flaws such as cracks formed in or just below a surface of a body to be detected are displayed using colors within different color regions in the color space when displaying, on the basis of a preset threshold value, the test signal ranging in magnitude from zero to the threshold value and the test signal falling in magnitude beyond the threshold value while changing the color and/or the depth of color little by little within each of the color regions according to the magnitude of the test signal. This enables small flaw signals, etc. to be displayed without exception, thereby preventing small flaws, etc. from being overlooked.

16 Claims, 12 Drawing Sheets

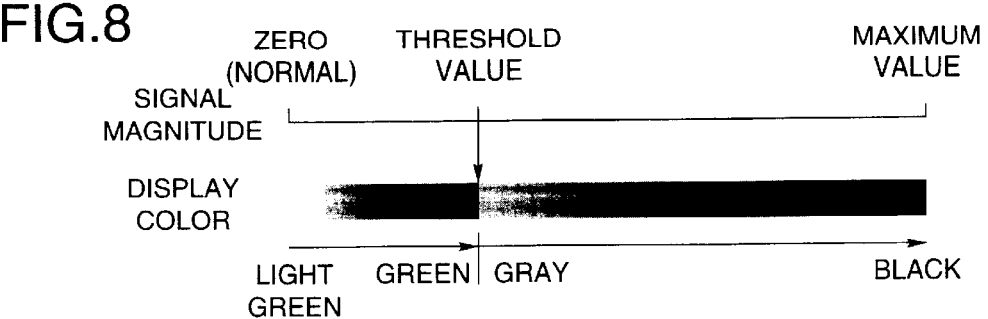
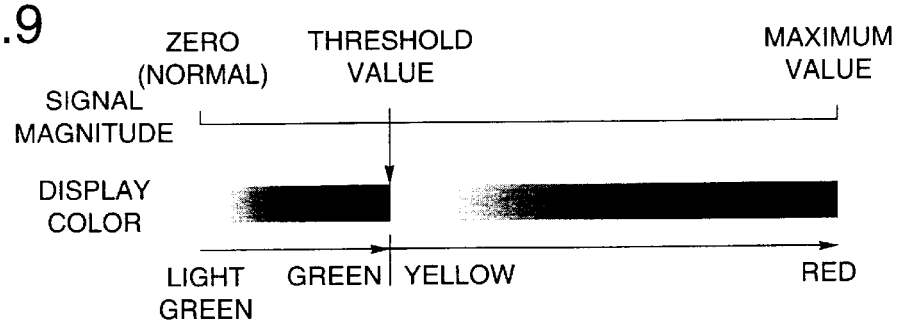
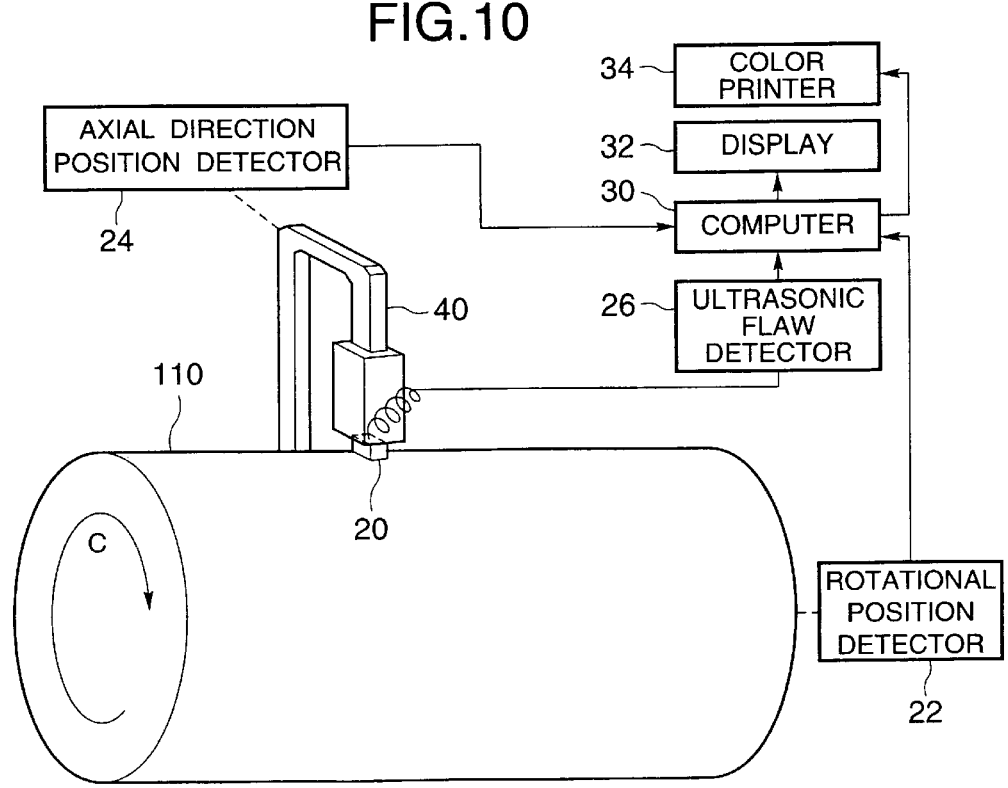

METHOD OF DISPLAYING SIGNAL OBTAINED BY MEASURING PROBE AND DEVICE THEREFOR

TECHNICAL FIELD

The present invention relates to a method of displaying a signal obtained by a measuring probe and a device therefor which is preferable to measure variables changing dependent upon a position of an object to be measured, by a measuring probe scanned on the object to be measured, and then display the measured values in a two-dimensional manner, and also the present invention includes a method of displaying surface flaw testing results and a device therefor which displays the magnitude of signals obtained by a surface flaw testing probe. In particular, the present invention relates to a method of displaying surface flaw testing results and a device therefor which is preferable to display the testing results of surface flaws such as cracks formed in or just below a surface of a cylindrical body of a metal such as a rolling roll, and a roller.

BACKGROUND ART

The flaws such as cracks formed in or just below a surface of a cylindrical body of a metal such as a rolling roll, and a roller are usually detected, as shown in FIG. 1, by putting a surface flaw testing probe (not shown) on a surface of a rotating cylindrical body 100, and then scanning the surface flaw testing probe in the axial direction of the cylindrical body to thereby carry out the flaw testing all over the surface of the cylindrical body. On this occasion, the above scanning is refereed to as "the spiral-scanning", because the locus which the surface flaw testing probe describes on the surface of the cylindrical body is, as shown in FIG. 1, shaped like a spiral having a pitch P which is dependent on a rotational speed of the cylindrical body and a feed speed of the probe.

Conventionally, the magnitude of signals obtained by the above-mentioned surface flaw testing probe is, as shown in FIG. 6 of Japanese provisional patent publication (Kokai) No.5-142215, displayed by scanning a surface flaw testing probe spirally on a rolling roll, comparing the amplitude of the signal with a predetermined threshold value while detecting the flaws, and displaying a black line, e.g. on a developed map of a roll when the amplitude of the signal is below the predetermined threshold value, or displaying no black line, e.g. on the developed map of the roll when beyond the predetermined threshold value to thereby discriminate the flaws.

However, the flaw-displaying method in Japanese Provisional Patent Publication (Kokai) No.5-142215 has a problem that so long as the amplitude of the signal does not reach the threshold value even if a small flaw signal is obtained, nothing is displayed. In other words, the threshold value is determined taking account of the amplitude of the flaw signal to be detected, the level of the detected signal obtained at a sound portion of the rolling roll, and the level of extraneous electric noise. Actually, the size and the shape of the surface flaw formed in the surface of the rolling roll are in a thousand different ways, thereby causing the magnitude of the flaw signal to change in great quantities. As a result, even if the flaw is so large as to be harmful, it may provide a small signal dependent on its shape.

On the other hand, setting the threshold value to a small value so as to detect the small flaw signal eliminates the overlook. However, the detected signals obtained at a sound portion of the rolling roll owing to the micro-structure or the surface roughness slightly differ with the rolling rolls, and also the extraneous electric noises vary according to the change of the working state of the electrical external equipment and the grounding state of the equipment which drives the surface flaw testing probe for detecting the flaws, which causes, if the magnitudes of the detected signals are high, the display to be made as if the flaws formed all over the surface of the roll.

Therefore, the threshold value is usually set with a margin with respect to the magnitude of the signal obtained at the sound portion of the rolling roll and the level of the extraneous electric noise (hereinafter generically referred to as ""the noise level""), and also so long as amplitude of the signal does not reach the threshold value even if a small flaw signal which is slightly higher than the noise level is obtained, nothing is displayed.

DISCLOSURE OF THE INVENTION

The present invention has been made in view of the above-mentioned conventional problems. It is therefore an object of the invention to display small flaw signals, etc. when displaying the magnitude of signals obtained by a measuring probe, e.g. a test signal obtained by a surface flaw testing probe.

The present invention provides a method of displaying a signal in a two-dimensional manner, in which signal is obtained by one or more measuring probes relatively scanned on an object to be measured, characterized by comprising the steps of setting an administrative range with respect to the magnitude of the signal, selecting respective display colors used for displaying a signal falling in magnitude beyond the administrative range and a signal falling in magnitude within the administrative range from at least two different color regions which can be visually distinguishable in the color space, and displaying the measured results using the selected respective display colors while changing the color and/or, the depth of color according to the magnitude of the signal, which causes the above-mentioned problems to be resolved.

The color space can be represented by an L*a*b model of CIEL (International Commission on Illumination), an RGB model, or a CMYK model.

In particular, when one of the at least two different color regions which can be visually distinguishable comprises a black-and-white gradation (gray scale), or two of the at least two different color regions which can be visually distinguishable are complementary in color to each other, the magnitude of the signal can be easily discriminated.

Further, when the signal falling in magnitude beyond the administrative range is displayed using the gray scale according to the magnitude of the signal, and the signal falling in magnitude within the administrative range is displayed using colors within the respective color regions except the gray scale while changing the color and/or the depth of color little by little according to the magnitude of the signal, the signal falling in magnitude within the administrative range and the signal falling in magnitude beyond the administrative range can be easily discriminated.

Besides, when the signal falling in magnitude beyond the administrative range is displayed using colors within the respective color regions except the gray scale while changing the color and/or the depth of color little by little according to the magnitude of the signal, and the signal falling in magnitude within the administrative range is displayed using the gray scale according to the magnitude of the signal, the signal of magnitude within the administrative range and the signal of magnitude beyond the administrative range can be easily discriminated.

Further, when both the signal falling in magnitude beyond the administrative range and the signal falling in magnitude within the administrative range are displayed using colors within color regions different from each other without using the gray scale while changing the color and/or the depth of color little by little according to the magnitude of the signal, any magnitude of the signal can be determined by colors.

The administrative range may have an upper limit value and a lower limit value, and it is possible to select three respective display colors used for displaying a signal ranging in magnitude from zero to the lower limit value, a signal ranging in magnitude from the lower limit value to the upper limit value, and a signal falling in magnitude beyond the upper limit value from at least three different color regions which can be visually distinguishable in the color space, and display the measured results using the selected respective display colors while changing the color and/or the depth of color according to the magnitude of the signal.

Or, the administrative range may comprise a greater part and a smaller part with respect to the threshold value, and it is possible to select respective display colors used for displaying a signal falling in magnitude ranging from zero to the threshold value, and a signal falling in magnitude beyond the threshold value from at least two different color regions which can be visually distinguishable in the color space, and display the measured results using the selected respective display colors while changing the color and/or the depth of color according to the magnitude of the signal.

Or, the signal ranging in magnitude from zero to the threshold value can be displayed using the gray scale according to the magnitude of the signal, and the signal falling in magnitude beyond the threshold value can be displayed using colors within the respective color regions except the gray scale while changing the color and/or the depth of color little by little according to the magnitude of the signal.

Or, the signal ranging in magnitude from zero to the threshold value can be displayed using colors within the respective color regions except the gray scale while changing the color and/or the depth of color little by little according to the magnitude of the signal, and the signal falling in magnitude beyond the threshold value can be displayed using the gray scale according to the magnitude of the signal.

Or, both the signal ranging in magnitude from zero to the threshold and the signal falling in magnitude beyond the threshold value can be displayed using colors within color regions different from each other without using the gray scale while changing the color and/or the depth of color little by little according to the magnitude of the signal.

The signal can be a signal obtained by a surface flaw testing probe.

The surface flaw testing probe can be a surface wave probe for detecting a flaw by receiving a echo from the flaw by use of surface waves propagated in a surface of the object, an eddy current testing probe for detecting a flaw by sensing the flaw-dependent change of an eddy current induced in a surface of the object, or a magnetic leakage flux sensor for detecting a flaw by sensing the flaw-dependent change of magnetic leakage flux.

The present invention provides a device for displaying a signal in a two-dimensional manner, in which signal is obtained by one or more measuring probes relatively scanned on an object to be measured, characterized by comprising a measuring probe relatively scanned on an object to be measured; a position detector of a measuring probe; a signal-processing device for processing a signal obtained by the measuring probe; and a computer, which enables the above-mentioned problems to be resolved.

The measuring probe can be a surface flaw testing probe, such as a surface wave probe, an eddy current testing probe, a magnetic leakage flux sensor.

According to the previously set administrative range, the computer can select respective display colors used for displaying a signal falling in magnitude beyond the administrative range and a signal falling in magnitude within the administrative range from at least two different color regions which can be visually distinguishable in the color space, and display the measured results while changing the color and/or the depth of color using colors within the respective color regions according to the magnitude of the signal.

In the present invention, the flaw testing results and the like are displayed using colors within different color regions selected from different color regions A to D as shown in FIGS. 2 to 4, which can be visually distinguishable in the color space when displaying, on the basis of a preset threshold value, the signal ranging in magnitude from zero to the threshold value and the signal falling in magnitude beyond the threshold value while changing the color and/or the depth of color little by little within each of the color regions according to the magnitude of the test signal. FIG. 2 shows a selection example of the different color regions in the color space, using a L*a*b color model of the CIE. FIG. 3 shows a selection example of the different color regions in the color space, using an RGB color model, and FIG. 4 shows a selection example of the different color regions in the color space, using a YMCK color model. In FIGS. 2 to 4, a color in the color region A comprises the depth of black-and-white color, i.e., the so-called gray scale, and the color regions B to D each comprises colors other than the gray scale.

For example, as shown in FIG. 5, the signal ranging in magnitude from zero to the threshold value is displayed using the gray scale (the color region A in FIGS. 2 to 4, e.g. a=0, and b=0 in the L*a*b color model of the CIE), i.e. the depth of color changing from white to black according to the magnitude of the signal, whereas the signal falling in magnitude beyond the threshold value is displayed using colors except the gray scale, e.g. colors from yellow to red (colors within the color regions except the color region A in FIGS. 2 to 4, e.g. a≠0, and B≠0 in the L*a*b color model of the CIE) while changing the color little by little according to the magnitude of the signal.

There is shown in FIG. 6 an example of thus displaying the flaw testing results on the developed map of the roll, and also in FIG. 7 an example of displaying the same flaw testing results by the conventional displaying method. Moreover, FIG. 7 shows the signal falling in magnitude beyond the threshold value by black color, and the signal ranging in magnitude from zero to the threshold value by white color, as is distinct from the case of Japanese Provisional Patent Publication (Kokai) No. 5-142215. This result is obtained from the rolling roll having artificial flaws and actual flaws in a surface thereof, by the spiral-scanning using the surface wave probe. FIG. 6 definitely shows that the small flaw signals, which have not been capable of being displayed by the conventional method, are clearly displayed. On this occasion, the reason why the displayed flaw is long in the circumferential direction is that the flaw is detected at plural times during the surface wave probe comes near the flaw.

Further, as shown in FIG. 8, the signal ranging in magnitude from zero to the threshold value can be displayed using color, e.g. from light green to green, within the respective color regions other than the gray scale according to the magnitude of the signal while changing the color and/or the depth of color little by little, and the signal falling in magnitude beyond the threshold value can be displayed using the gray scale, e.g. the depth of color changing from gray to black according to the height of the magnitude of the signal. Also as shown in FIG. 9, both the signal ranging in magnitude from zero to the threshold value and the signal falling in magnitude beyond the threshold value can be displayed using colors, e.g. from light green to green for the former, and from yellow to red for the latter, within color regions different from each other without using the gray color while changing the color and the depth of color little by little according to the magnitude of the signal.

Moreover, FIGS. 2 to 4 show three types of color models for expressing the color space; however, the color space-expressing method using the color model is not limited to the above three types. Different type of color models can be employed.

BRIEF DESCRIPTION OF THE DRAWINGS

FIG. 8 is a view showing another example of the relationship between the signal magnitude and the display color;

FIG. 9 is a view showing further another example of the same;

FIG. 10 is a perspective view, a part of which is a block diagram, showing a general arrangement of a first embodiment of the present invention;

BEST MODE FOR CONDUCTING THE PRESENT INVENTION

Figure 1:
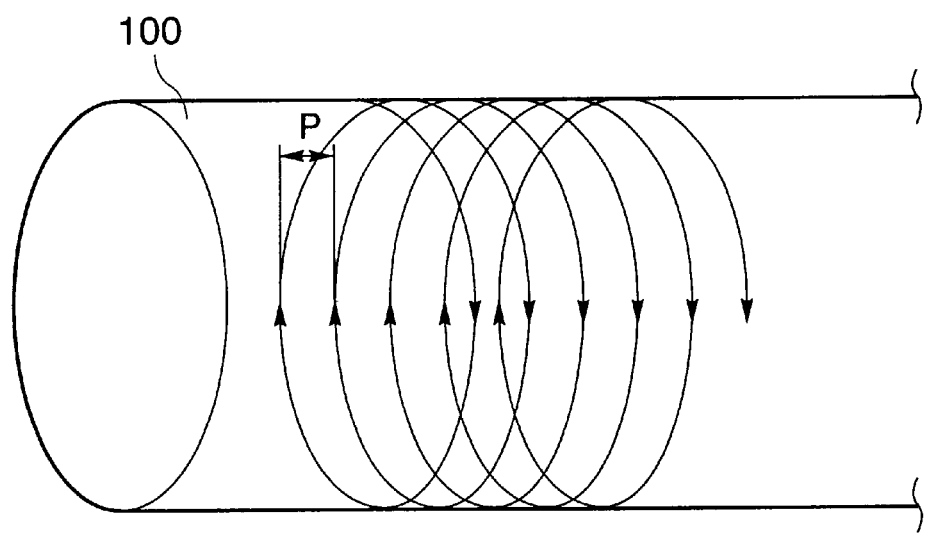
FIG. 1 is a plan view showing a state in which a surface wave probe is scanned on a surface of a cylindrical body.

The inventions will now be described in detail with reference to the drawings showing respective embodiments thereof.

In a first embodiment of the invention, a probe 20 for use in surface flaw testing comprises a surface wave probe which detects a flaw by propagating a surface wave in a surface of an object and receiving a flaw echo. Even if a flaw testing probe 20 comprises an eddy current test probe or a magnetic leakage flux sensor, the present invention method of displaying flaw positions and flaw signal magnitudes on the developed map of a roll can be applied thereto.

The present embodiment comprises, as shown in FIG. 10, a roll-rotating device (not shown), a rotational position detector 22, a probe 20, an axial position detector 24 for detecting a position of the probe 20 in an axial direction of a rolling roll, an ultrasonic flaw detector 26, a computer 30, a display 32, a color printer 34, and a holding device 40 of the probe 20.

The roll-rotating device is capable of rotating the rolling roll 110, which is subjected to a surface flaw testing, in the circumferential direction C. This rotating device needs only to be constructed by a well-known suitable device which is not shown in the drawing for the purpose of preventing the drawing from becoming complicated. The rotational position of the rolling roll 110 rotated by the roll-rotating device is detected by the rotational position detector 22 and then sent to the computer 30.

The probe 20 is capable of forming a water gap between its surface and the rolling roll 110, which is subjected to a surface flaw testing, and hence propagating the surface wave in the surface of the rolling roll 110 to thereby detect a surface flaw in the rolling roll 110.

The probe 20 is connected to the ultrasonic flaw detector 26 which amplifies a signal obtained by the probe 20 to a predetermined level, extracts the flaw echo, and then detects the amplitude of the flaw echo to thereby output the detected amplitude to the computer 30.

The probe 20 is attached to the holding device 40, a detail structure of which is described later, and hence held thereon so as to be scanned for flaw testing while keeping a constant distance with the rolling roll 110. Therefore, rotating the rolling roll 110 by a roll-rotating device (not shown) while scanning the holding device 40 in an axial direction of the rolling roll 110 by a suitable driving device (not shown) scans the probe 20 spirally on the rolling roll 110, thereby enabling all the surface of the rolling roll 110 to be tested. A position of the probe 20 in the axial direction of the rolling roll 110 is detected by the axial position detector 24 and hence sent to the computer 30.

Figure 2:
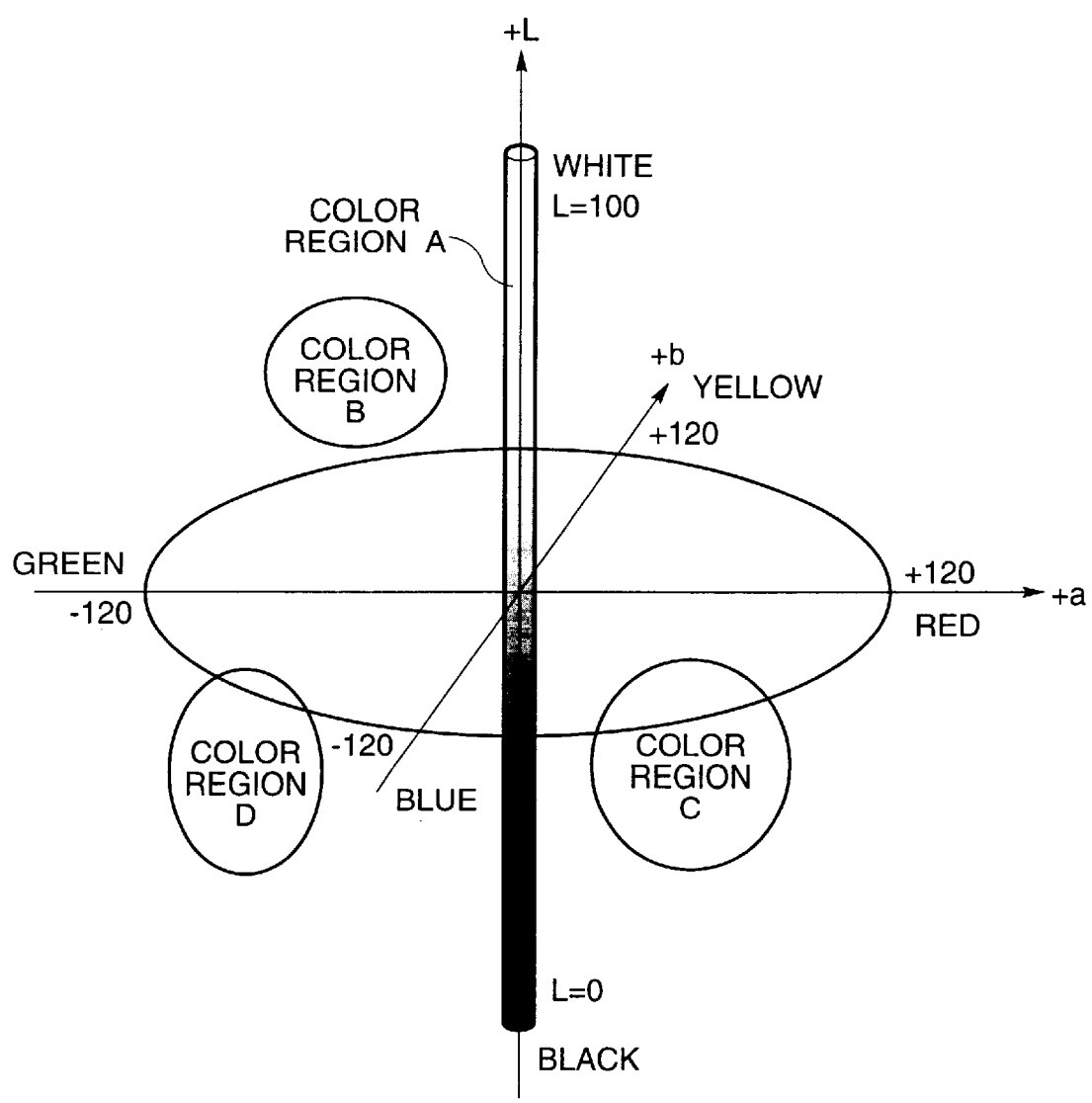
FIG. 2 is an explanatory view useful in explaining the principle of the present invention, which shows different color regions in an L*a*b color model of CIE.
Figure 3:
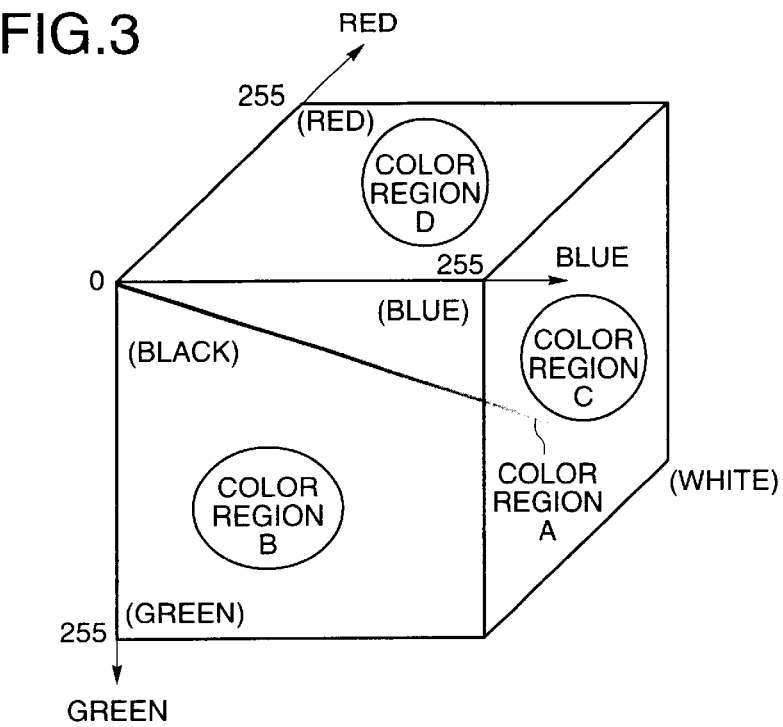
FIG. 3 is an explanatory view of the same, which shows different color regions in an RGB color model.
Figure 4:
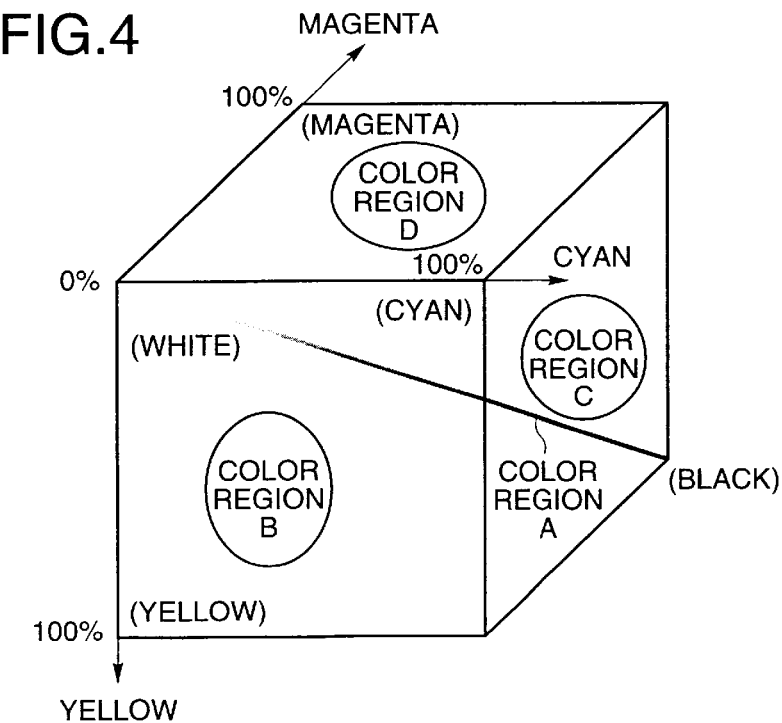
FIG. 4 is an explanatory view of the same, which shows different color regions in an CMYK color model.
Figure 5:
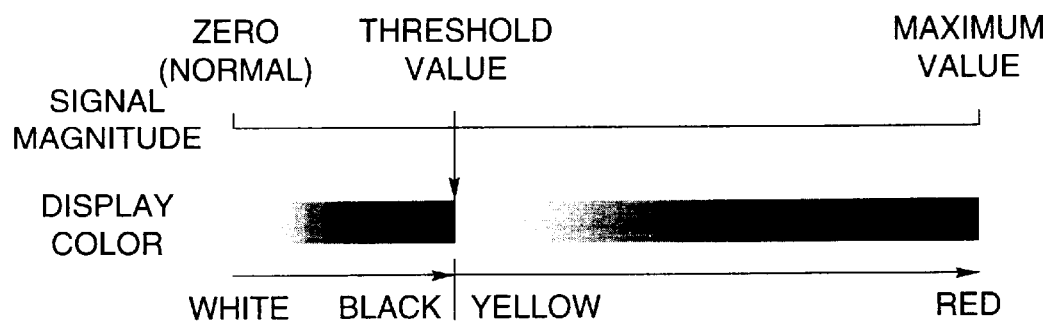
FIG. 5 is a view showing an example of the relationship between the signal magnitude and the display color according to the present invention.
Figure 6:
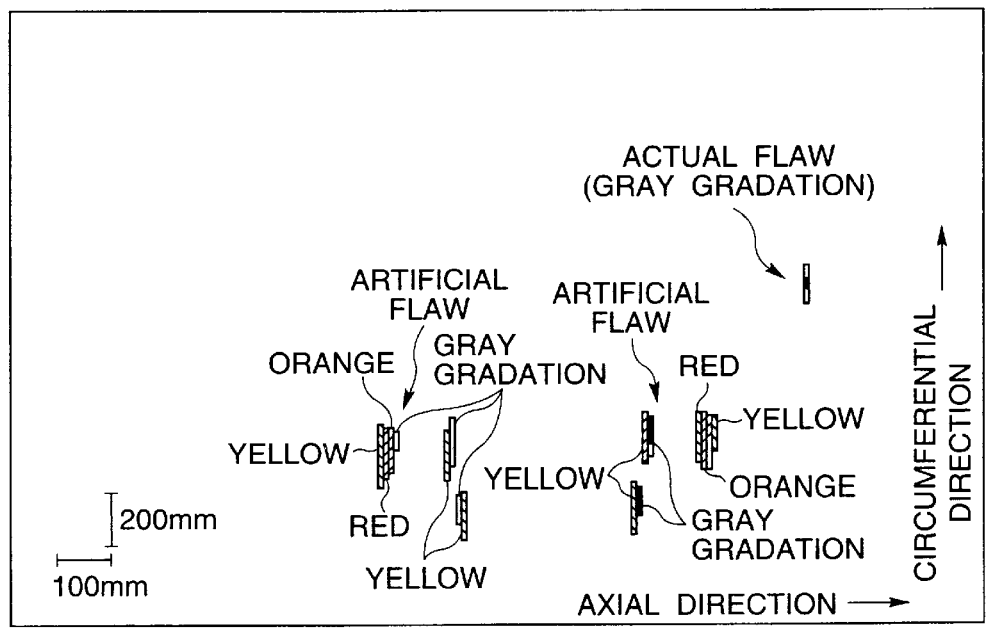
FIG. 6 is a view showing an example of the flaw testing results displayed by the present invention method.
Figure 7:
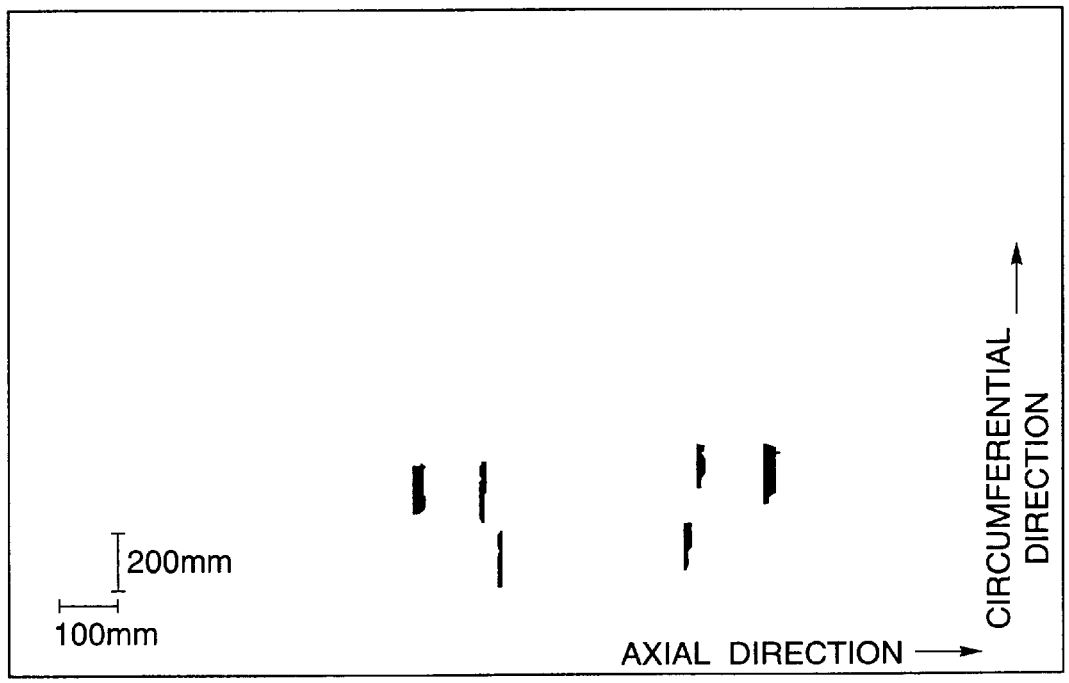
FIG. 7 is a view showing an example of the flaw testing results displayed by the conventional method.

The computer 30 receives, during the spiral-scanning, a signal of a rotational position of the rolling roll 110 detected by the rotational position detector 22, a signal of a position of the probe 20 in the axial direction of the rolling roll 110 detected by the axial position detector 24, and an amplitude of the signal detected by the ultrasonic flaw detector 26, and then causes the display 32 to display the flaw testing results on the developed map of the roll. On this occasion, according to the invention, the flaws are displayed according to the amplitude of the signal detected by the ultrasonic flaw detector 26, in concrete terms using colors within different color regions in the color space as shown in FIGS. 2 to 4, when displaying, on the basis of a preset threshold value, the signal ranging in magnitude from zero to the threshold value and the signal falling in magnitude beyond the threshold value while changing the color and/or the depth of color little by little within each of the color regions according to the magnitude of the signal. Further, the flaw testing results displayed on the developed map of the roll is sent to and then printed on the color printer 34.

Figure 11:
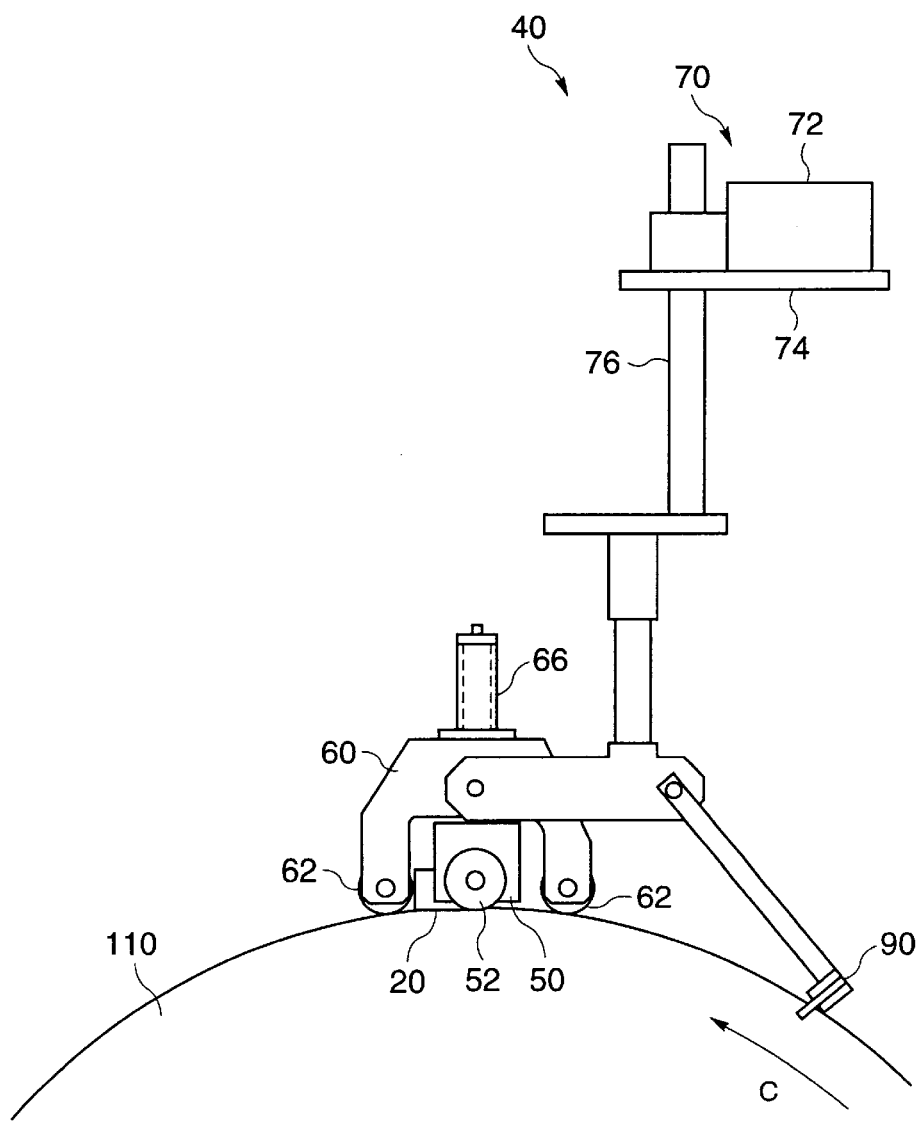
FIG. 11 is a detailed front view of a holding device for a surface wave probe in the first embodiment.
Figure 12:
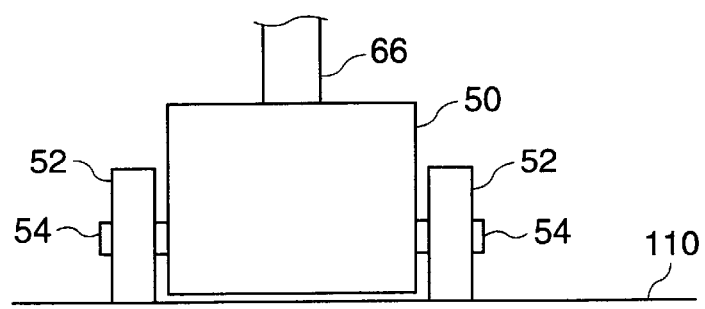
FIG. 12 is a side view showing a part of the probe holding device of the same.

The structure of the holding device 40 will be described in detail with reference to FIGS. 11 to 13.

The holding device 40 includes a probe holder 50. The probe holder 50 is disposed on a holding mechanism 60 attached to a lower portion of a guide 76 which is slidable to a fixing structure 70 located above the rolling roll 110. The holding mechanism 60 is provided with a pair of fore rollers 62 and a pair of rear rollers 62, i.e. total four rollers 62. When carrying out the flaw testing, these rollers 62 are contacted with the surface of the rolling roll 110 and further rotated, thereby stabilizing the flaw testing. The probe holder 50 is attached to a portion between two pairs of the four rollers 62.

The fixing mechanism 70 is provided with a motor 72 for supplying a power of lifting and lowering the holding mechanism 60 along the guide 76, and a motor-attaching table 74. The power of the motor 72 needs only to be transmitted by a conventionally well-known suitable means which is not shown in the drawing for the purpose of preventing the drawing from becoming complicated.

Disposed on a front side (right-hand in the drawing) of the holding mechanism 60 is a scraper 90 for removing the coupling medium deposited on the surface of the rolling roll 110 in such a manner that the remaining coupling medium does not flow into the surface wave-propagating path.

The probe holder 50 is supported on the holding mechanism 60 with a resilient body such as a spring interposed therebetween so that the probe holder 50 is urged to the surface of the rolling roll 110. In detail, the probe holder 50 is attached to a leading end of a bar-like body 66 fitted to the holding mechanism 60 with a play slidably up and down, and a spring (not shown) is disposed around the bar-like body 66 at a suitable location, thereby causing the probe holder 50 to be permanently urged downward.

The probe 20 is disposed on the probe holder 50, and then a pair of following rollers 52 are disposed protrusively on a side of the rolling roll 110 located below the probe 20, for forming a predetermined gap between the probe 20 and the rolling roll 110. In concrete terms, as shown in FIG. 12, a shaft 54 is disposed horizontally on the probe holder 50, and then the following rollers 52 are disposed on the shaft 54.

In this way, the following rollers 52 rotatably supported on the probe holder 50 are urged by the spring to thereby permanently contact with the surface of the rolling roll 110. According to this structure, the probe holder 50 holds the probe 20 so as to maintain the gap between the probe 20 and the rolling roll 110 at a constant value.

Figure 13:
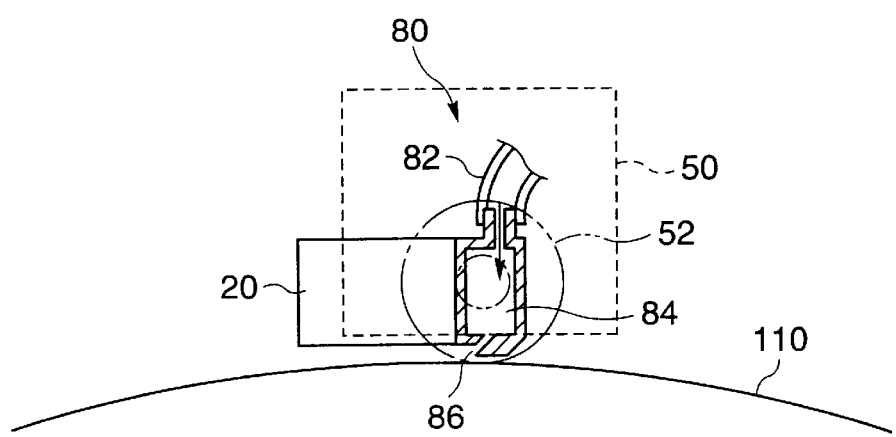
FIG. 13 is a side view showing a feed water device of the same.

As shown in FIG. 13 in detail, a feed water device 80 is disposed inside the probe holder 50. The feed water device 80 once contains water led from a pipe 82 in a storing portion 84, discharges the water through a discharging port 86 disposed on a bottom of the storing portion 84, and then forms a no-bubble water layer between the probe 20 and the rolling roll 110. The feed water device 80 needs only to be constructed by a conventionally well-known suitable means, a detail description of which is therefore omitted.

Figure 14:
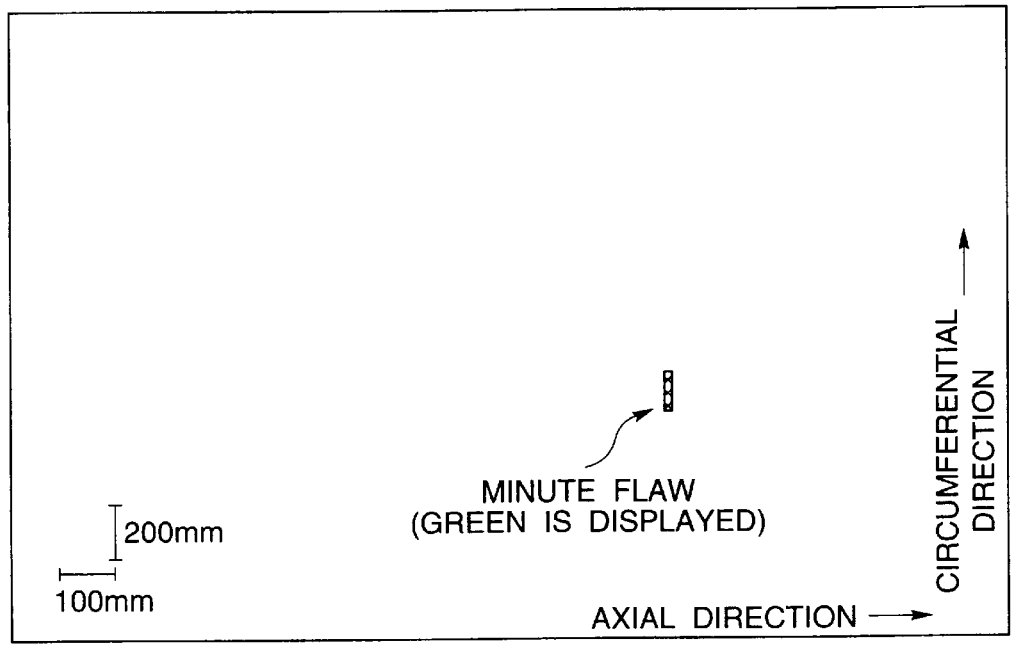
FIG. 14 is a developed map of a roll showing a display example of the flaw testing results according to the first embodiment.

Thus constructed flaw testing device detects minute surface flaws in the rolling roll 110, and then the flaw testing results are shown on the developed map of the roll of FIG. 14 using display colors shown in FIG. 9. This enables the small flaw signals, which have not been capable of being displayed by the conventional method, to be clearly displayed.

Moreover, the present invention is not limited to the above embodiment in which it is applied to the surface flaw testing of the rolling roll, but it is apparent that the present invention can be applied to the display of the results of the surface flaw testing for the cylindrical bodies other than the rolling roll and the body having a shape other than the cylinder.

Figure 15:
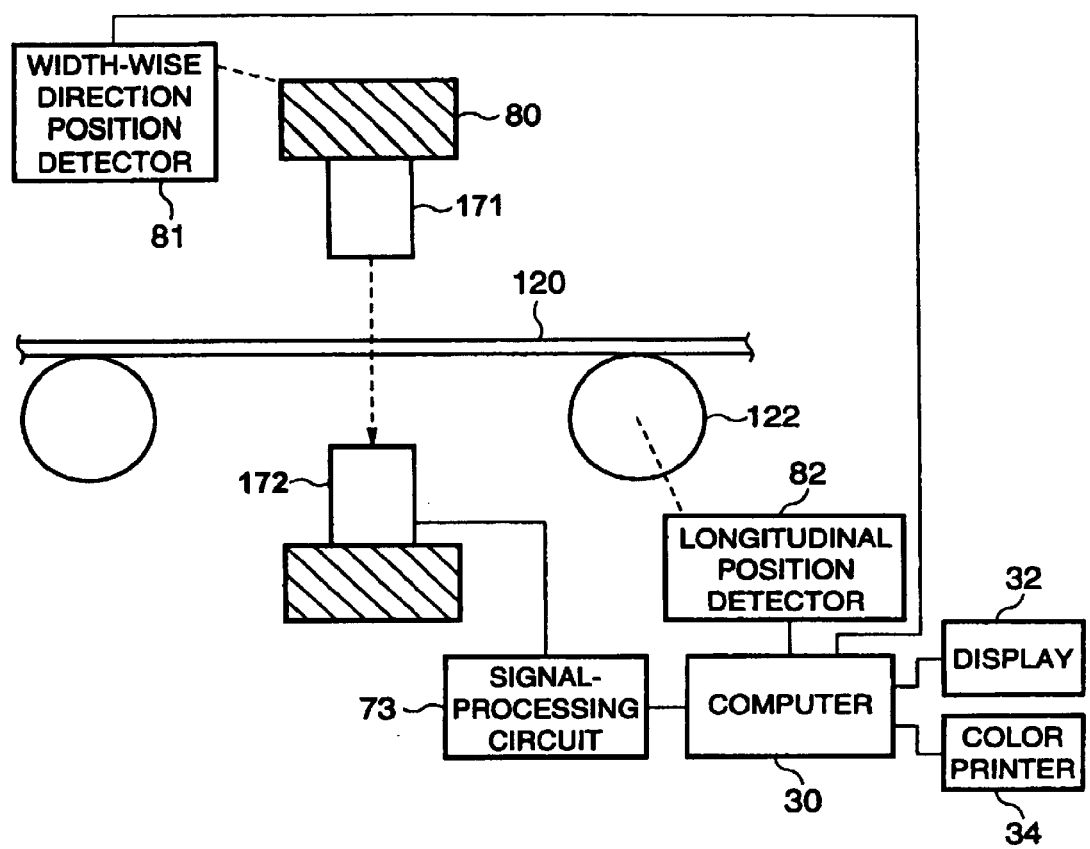
FIG. 15 is a side view, apart of which is a block diagram, showing the structure of a second embodiment of the present invention.
Figure 16:
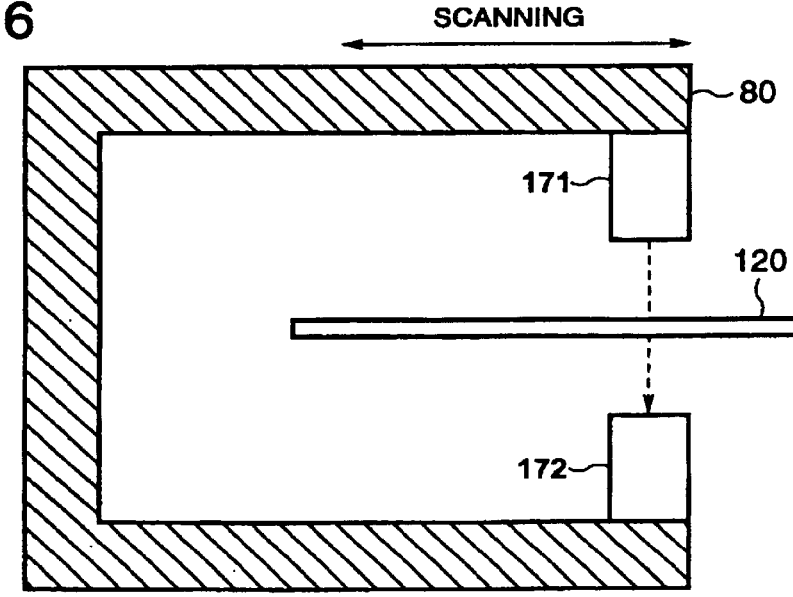
FIG. 16 is a sectional view of a main part of the same.

Further, FIG. 15 (side view) and FIG. 16 (sectional view of a main part) show a second embodiment of the present invention. In this embodiment, the present invention is applied to display of the measured thickness of a steel sheet 120 in a two-dimensional manner on the transporting or rolling line while transporting or rolling the steel sheet 120 by transporting rollers 122 and scanning a radiation thickness gauge in the width-wise direction.

This embodiment has, as shown in FIG. 15 and 16, a radiation source 171, a radiation detector 172 (both the radiation source 171 and the radiation detector 172 are referred generically to as "the radiation-measuring head"), a width-wise direction position detector 81 of the radiation-measuring head, a longitudinal position detector 82 for detecting a position of an object to be measured in the transporting or rolling direction of the steel sheet 120, a signal processing circuit 73, a computer 30, a display 32, a color printer 34, and a scanning device 80 for scanning the radiation-measuring head on the steel sheet in the width-wise direction.

The transporting rollers 122 are capable of transporting the steel sheet 120, of which thickness is to be measured, in a predetermined direction. The transporting rollers 122 needs only to be constructed by a well-known suitable device, so that the driving device and the supporting means are not shown in the drawing for the purpose of preventing the drawing for becoming complicated. The longitudinal position of the steel sheet 120 transported by the transporting rollers 122 is detected by the longitudinal position detector 82 such as a rotary encoder, for measuring the travelling distance from rotation of the transporting roller 122, and then sent to the computer 30.

In the radiation-measuring head, the radiation detector 172 detects the dose of the radiation irradiated by the radiation source 171 and penetrating through the steel sheet 120, thereby enabling the attenuation of the radiation penetrating through the steel sheet to be detected, which enables the thickness of the steel sheet to be detected.

Connected to the radiation-measuring head is a signal-processing circuit 73. The signal-processing circuit 73 amplifies a signal detected by the radiation detector 172 to a predetermined level, detects the amplitude of the signal, and outputs it to the computer 30.

The radiation-measuring head is attached to and held on the scanning device 80 in such a manner that the radiation source 171 and the radiation detector 172 can be scanned on the steel sheet 120 with a constant distance being kept therewith. Therefore, during the transportation of the steel sheet 120, scanning the scanning device 80 in the widthwise direction of the steel sheet 120 by a suitable driving device (not shown) scans the radiation-measuring head on the steel sheet 120 in a zigzag manner, thereby enabling the thickness of the steel sheet 120 to be measured all over the steel sheet 120. A position of the radiation-measuring head in the width-wise direction of the steel sheet 120 is detected by the width-wise direction detector 81, and then sent to the computer 30.

The computer 30 receives, during the scanning in the zigzag manner, a signal related to a position of the radiation-measuring head in the width-wise direction of the steel sheet 120 detected by the width-wise direction position detector 81, a signal related to a position of the radiation-measuring head in the longitudinal direction of the steel sheet 120 detected by the longitudinal position detector 82, and a signal related to the dose of the penetrating radiation detected by the signal processing circuit 73, and then causes the display 32 to display the measured results of the thickness of the steel sheet 120 in a two-dimensional manner. On this occasion, according to the invention, the thickness is displayed according to the dose of the penetrating radiation detected by the signal processing circuit73, in concrete terms, using colors within different color regions B, C, and D as shown in FIGS. 2 to 4, when displaying, on the basis of an upper limit value and a lower limit value of a preset administrative range, the thickness ranging in magnitude from zero to the lower limit value, the thickness ranging in magnitude from the lower limit value to the upper limit value, and the thickness falling more than the upper limit value, while changing the color and/or the depth of color little by little within each of the color regions according to the thickness. Further, the steel sheet thickness-measured results displayed in a two-dimensional manner is sent to and then printed on the color printer 34.

Figure 17:
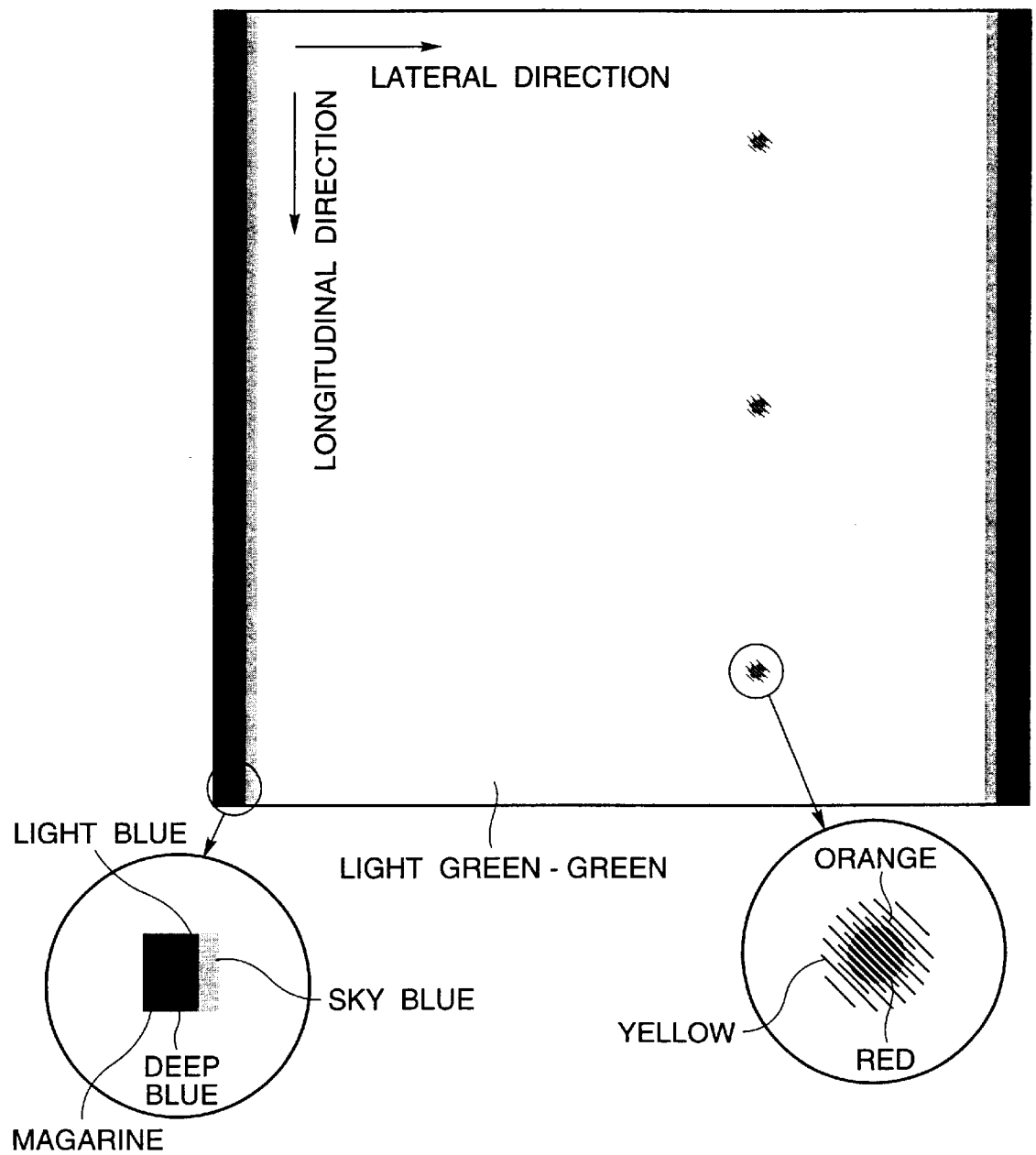
FIG. 17 is a view showing a display example of the thickness-measured results of a steel sheet according to the second embodiment.

Thus constructed thickness-measuring device measures the thickness of the steel sheet in a two-dimensional manner, which steel sheet has high spots caused by the pit formed by the external force in the surface of the roll, and then the measured results are shown in FIG. 17. FIG. 17 understandably shows the high spots, which have been overlooked by only observation of the thickness profile, and also clearly shows even the occurrence period.

Industrial Availability

According to the present invention, small flaw signals, etc., which have been neglected, can be displayed without exception.

What is claimed is:

1. A method of displaying a probe signal in a two-dimensional manner, in which said probe signal is obtained by one or more measuring probes relatively scanned on an object to be measured, the method comprising:

setting an administrative range with respect to a magnitude of said probe signal, the administrative range having a first part and a second part, the first part and the second part being divided by a threshold value;

selecting a display color from a first color region when said probe signal has a magnitude corresponding to the first part of said administrative range, and selecting a display color from a second color region that differs from the first color region, and which is visually distinguishable from said first color region in a color space, when said probe signal has a magnitude corresponding to the second part of said administrative range; and displaying a result of measurement using said selected respective display colors in changing colors and/or depths of color and/or changing intensity of darkness according to said magnitude of said probe signal, such that a plurality of different colors and/or depths of color and/or changing intensity of darkness from each of the first and second color regions are displayed, wherein one of said first and second color regions comprises a gray scale, said probe signal having a magnitude corresponding to one of the first part and the second part of said administrative range is displayed using said gray scale in changing intensity of darkness according to said magnitude of said probe signal, and said probe signal having a magnitude corresponding to the other one of the first part and the second part of said administrative range is displayed using colors within said second color region, said second color region being a color region other than said gray scale, in changing colors and/or depths of color according to said magnitude of said probe signal.

2. A method of displaying a probe signal obtained by one or more measuring probes, as claimed in claim 1, wherein said color space is represented by an L*a*b model of CIE (International commission on Illumination).

3. A method of displaying a probe signal obtained by one or more measuring probes, as claimed in claim 1, wherein said color space is represented by an RGB model.

4. A method of displaying a probe signal obtained by one or more measuring probes, as claimed in claim 1, wherein said color space is represented by a CMYK model.

5. A method of displaying a signal obtained by one or more measuring probes, as claimed in claim 1, wherein said probe signal having a magnitude from zero to said threshold value is displayed using gray scale according to said magnitude of said probe signal, such that different levels of said gray scale are displayed, and said probe signal having a magnitude above said threshold value is displayed using colors within said first color region, said first color region being a color region other than said gray scale, in changing colors and/or depths of color according to said magnitude of said probe signal, such that a plurality of different colors and/or depths of color from the first color region are displayed.

6. A method of displaying a signal obtained by one or more measuring probes, as claimed in claim 1, wherein said probe signal having a magnitude from zero to said threshold value is displayed using colors within said second color region, said second color region being a color region other than gray scale, in changing colors and/or depths of color according to said magnitude of said probe signal, such that a plurality of different colors and/or depths of color from the second color region are displayed, and said probe signal having a magnitude above said threshold value is displayed using gray scale according to said magnitude of said signal, such that different levels of said gray scale are displayed.

7. A method of displaying a signal obtained by one or more measuring probes, as claimed in claim 1, wherein said probe signal comprises a signal obtained by a surface flaw testing probe.

8. A method of displaying a signal obtained by one or more measuring probe, as claimed in claim 7, wherein said surface flaw testing probe comprises a surface wave probe that detects a flaw by receiving a echo from said flaw using a surface wave propagated in a surface of said object.

9. A method of displaying a signal obtained by one or more measuring probes, as claimed in claim 7, wherein said surface flaw testing probe comprises an eddy current testing probe that detects a flaw by sensing a flaw-dependent change of an eddy current induced in a surface of said object.

10. A method of displaying a signal obtained by one or more measuring probes, as claimed in claim 7, wherein said surface flaw testing probe comprises a magnetic leakage flux sensor that detects a flaw by sensing a flaw-dependent change of magnetic leakage flux.

11. A method of displaying a probe signal in a two-dimensional manner, in which said probe signal is obtained by one or more measuring probes relatively scanned on an object to be measured, the method comprising:

setting an administrative range with respect to a magnitude of said probe signal, said administrative range having a first limit value and a second limit value;

selecting a display color from a first color region when said probe signal has a magnitude from zero to said second limit value, selecting a display color from a second color region when said probe signal has a magnitude from said second limit value to said first limit value, and selecting a display color from a third color region when said probe signal has a magnitude above said first limit value, said first, second and third color regions differing from each other and being visually distinguishable from each other in the color space; and displaying a result of measurement using said selected respective display colors in changing colors and/or depths of color and/or intensity of darkness according to said magnitude of said signal, such that a plurality of different colors and/or depths of color and/or intensity of darkness from each of the first, second and third color regions are displayed, wherein one of said first, second and third color regions comprises a gray scale which is displayed in changing intensity of darkness.

12. A device for displaying a signal in a two-dimensional manner, in which signal is obtained by one or more measuring probes relatively scanned on an object to be measured, comprising;

a measuring probe relatively scanned on an object to be measured;

a measuring probe position detector that transmits a position signal of the measurement probe to a computer; and a signal-processing device that processes a probe signal obtained by said measuring probe and transmits said probe signal to the computer;

wherein an administrative range is set with respect to a magnitude of said probe signal, the administrative range having a first part and a second part, the first part and the second part being divided by a threshold value, and the computer selects a display color from a first color region when said probe signal has a magnitude corresponding to the first part of said administrative range, and selects a display color from a second color region that differs from the first color region, and which is visually distinguishable from said first color region in a color space, when said probe signal has a magnitude corresponding to the second part of said administrative range, and causes a result of measurement to be displayed using said selected respective display colors in changing colors and/or depths of color and/or intensity of darkness according to said magnitude of said probe signal, such that a plurality of different colors and/or depths of color and/or intensity of color from each of the first and second color regions are displayed, one of said first and second color regions comprises a gray scale, said probe signal having a magnitude corresponding to one of the first part and the second part of said administrative range is displayed using said gray scale in changing intensity of darkness according to said magnitude of said probe signal, and said probe signal having a magnitude corresponding to the other one of the first part and the second part of said administrative range is displayed using colors within said second color region, said second color region being a color region other than said gray scale, in changing colors and/or depths of color according to said magnitude of said probe signal.

13. A device for displaying a signal obtained by one or more measuring probes, as claimed in claim 12, wherein said measuring probe comprises a surface flaw testing probe.

14. A device for displaying a signal obtained by one or more measuring probes, as claimed in claim 13, wherein said surface flaw testing probe comprises a surface wave probe that detects a flaw by receiving an echo from said flaw using a surface wave propagated in a surface of said object.

15. A device for displaying a signal obtained by one or more measuring probes, as claimed in claim 13, wherein said surface flaw testing probe comprises an eddy current testing probe that detects a surface flaw by sensing a flaw-dependent change of an eddy current induced in a surface of said object.

16. A device for displaying a signal obtained by one or more measuring probe, as claimed in claim 13, wherein said surface flaw testing probe comprises a magnetic leakage flux sensor that detects a flaw by sensing a flaw-dependent change of magnetic leakage flux.

* * * * *